(12) United States Patent
Moore (10) Patent No.: US 10,276,029 B2
(45) Date of Patent: Apr. 30, 2019

(54) METHODS AND SYSTEMS FOR OBTAINING MORE ACCURATE COMPLIANCE METRICS

(71) Applicant: GOJO Industries, Inc., Akron, OH (US)

(72) Inventor: Mark W. Moore, Aurora, OH (US)

(73) Assignee: GOJO Industries, Inc., Akron, OH (US)

( * ) Notice: Subject to any disclaimer, the term of this patent is extended or adjusted under 35 U.S.C. 154(b) by 35 days.

(21) Appl. No.: 14/938,269

(22) Filed: Nov. 11, 2015

(65) Prior Publication Data

US 2016/0140832 A1    May 19, 2016

Related U.S. Application Data

(60) Provisional application No. 62/079,205, filed on Nov. 13, 2014.

(51) Int. Cl.
*G08B 23/00* (2006.01)
*G08B 21/24* (2006.01)
*G16H 40/20* (2018.01)

(52) U.S. Cl.
CPC .......... *G08B 21/245* (2013.01); *G16H 40/20* (2018.01)

(58) Field of Classification Search
None
See application file for complete search history.

(56) References Cited

U.S. PATENT DOCUMENTS

| | | |
|---|---|---|
| 4,746,907 A | 5/1988 | Zehnder, Jr. |
| 5,042,091 A | 8/1991 | Tonkens |
| 5,884,808 A | 3/1999 | Muderlak et al. |
| 5,941,363 A | 8/1999 | Partyka et al. |
| 6,236,317 B1 | 5/2001 | Cohen et al. |
| 6,278,372 B1 | 8/2001 | Velasco, Jr. et al. |
| 6,344,794 B1 | 2/2002 | Ulrich et al. |
| 6,360,181 B1 | 3/2002 | Gemmell et al. |
| 6,392,546 B1 | 5/2002 | Smith |
| 6,404,837 B1 | 6/2002 | Thompson |
| 6,462,656 B2 | 10/2002 | Ulrich et al. |
| 6,539,393 B1 | 3/2003 | Kabala |

(Continued)

FOREIGN PATENT DOCUMENTS

WO    9933008    7/1999

OTHER PUBLICATIONS

Joint Commision, Measuring Hand Hygiene Adherence: Overcoming the Challenges, 2009.*

(Continued)

*Primary Examiner* — James J Yang
*Assistant Examiner* — Kevin Lau
(74) *Attorney, Agent, or Firm* — Calfee, Halter & Griswold LLP (57) ABSTRACT

Exemplary embodiments of methodologies of obtaining more accurate compliance metrics are disclosed herein. An exemplary method of determining a compliance metric includes determining a number of dispense events and determining a number of opportunities for obtaining dispense events. The number of opportunities for obtaining dispense events is a function of the time between an entry event and a exit event, in addition, the compliance metric is a function of the number of dispense events and the number of opportunities.

17 Claims, 4 Drawing Sheets

(56) References Cited

U.S. PATENT DOCUMENTS

| | | | |
|---|---|---|---|
| 6,542,568 B1 | 4/2003 | Howes, Jr. et al. |
| 6,622,088 B2 | 9/2003 | Hood |
| 6,727,818 B1 | 4/2004 | Wildman et al. |
| 6,825,763 B2 | 11/2004 | Ulrich et al. |
| 6,876,303 B2 | 4/2005 | Reeder et al. |
| 6,958,706 B2 | 10/2005 | Chaco et al. |
| 6,972,683 B2 | 12/2005 | Lestienne et al. |
| 7,015,816 B2 | 3/2006 | Wildman et al. |
| 7,042,337 B2 | 5/2006 | Borders et al. |
| 7,080,061 B2 | 7/2006 | Kabala |
| 7,154,397 B2 | 12/2006 | Zerhusen et al. |
| 7,242,306 B2 | 7/2007 | Wildman et al. |
| 7,242,307 B1 | 7/2007 | Leblond et al. |
| 7,248,933 B2 | 7/2007 | Wildman |
| 7,271,728 B2 | 9/2007 | Taylor et al. |
| 7,286,057 B2 | 10/2007 | Boiling |
| 7,408,470 B2 | 8/2008 | Wildman et al. |
| 7,423,533 B1 | 9/2008 | Leblond et al. |
| 7,443,302 B2 | 10/2008 | Reeder et al. |
| 7,443,303 B2 | 10/2008 | Spear et al. |
| 7,450,024 B2 | 11/2008 | Wildman et al. |
| 7,679,520 B2 | 3/2010 | Zerhusen et al. |
| 7,734,476 B2 | 6/2010 | Wildman et al. |
| 7,812,730 B2 | 10/2010 | Wildman et al. |
| 7,855,651 B2 | 12/2010 | Leblond et al. |
| 7,907,053 B2 | 3/2011 | Wildman et al. |
| 7,911,249 B2 | 3/2011 | Wada |
| 8,011,458 B2 | 9/2011 | Hauser |
| 8,026,821 B2 | 9/2011 | Reeder et al. |
| 8,085,155 B2 | 12/2011 | Prodanovich et al. |
| 8,094,029 B2 | 1/2012 | Ortiz et al. |
| 8,258,965 B2 | 9/2012 | Reeder et al. |
| 8,334,779 B2 | 12/2012 | Zerhusen et al. |
| 8,368,544 B2 | 2/2013 | Wildman et al. |
| 8,368,545 B2 | 2/2013 | Zerhusen et al. |
| 8,395,515 B2 | 3/2013 | Tokhtuev et al. |
| 8,427,323 B2 | 4/2013 | Alper et al. |
| 8,460,223 B2 | 6/2013 | Huster et al. |
| 8,487,774 B2 | 7/2013 | Reeder et al. |
| 8,502,680 B2 | 8/2013 | Tokhtuev et al. |
| 8,502,681 B2 | 8/2013 | Boiling |
| 8,558,660 B2 | 10/2013 | Nix et al. |
| 8,558,701 B2 | 10/2013 | Wegelin et al. |
| 8,564,431 B2 | 10/2013 | Snodgrass |
| 8,572,778 B2 | 11/2013 | Newkirk et al. |
| 8,598,996 B2 | 12/2013 | Wildman et al. |
| 8,674,839 B2 | 3/2014 | Zerhusen et al. |
| 8,674,840 B2 | 3/2014 | Snodgrass |
| 8,698,637 B2 | 4/2014 | Raichman |
| 8,766,804 B2 | 7/2014 | Reeder et al. |
| 8,779,924 B2 | 7/2014 | Pesot et al. |
| 8,847,752 B2 | 9/2014 | Wegelin et al. |
| 8,872,665 B2 | 10/2014 | Snodgrass |
| 8,917,166 B2 | 12/2014 | Collins, Jr. et al. |
| 9,349,267 B2 | 5/2016 | Wildman et al. |
| 9,349,274 B2 | 5/2016 | Wegelin et al. |
| 9,396,638 B2 | 7/2016 | Wildman et al. |
| 9,672,726 B2 | 6/2017 | Borke |
| 9,715,817 B2 | 7/2017 | Wildman et al. |
| 2003/0163434 A1 | 8/2003 | Barends |
| 2003/0176207 A1 | 9/2003 | Yamagishi |
| 2004/0090333 A1* | 5/2004 | Wildman ............ G06F 19/3418 340/573.1 |
| 2005/0043011 A1 | 2/2005 | Murray et al. |
| 2005/0151641 A1 | 7/2005 | Ulrich et al. |
| 2005/0248461 A1 | 11/2005 | Lane |
| 2008/0140515 A1 | 6/2008 | Godwin |
| 2008/0149515 A1 | 6/2008 | Godwin |
| 2008/0185399 A1 | 8/2008 | Yang et al. |
| 2009/0091458 A1 | 4/2009 | Deutsch |
| 2009/0188033 A1 | 7/2009 | Honsa |
| 2009/0324444 A1 | 12/2009 | Stratmann |
| 2010/0262430 A1* | 10/2010 | Gips ..................... G06F 19/327 705/2 |
| 2010/0315244 A1* | 12/2010 | Tokhtuev ............... G06Q 10/00 340/603 |
| 2011/0316701 A1* | 12/2011 | Alper .................. G08B 21/245 340/573.1 |
| 2012/0154582 A1 | 6/2012 | Johnson et al. |
| 2012/0158419 A1 | 6/2012 | Nuthi |
| 2012/0329438 A1 | 12/2012 | Snodgrass |
| 2013/0113619 A1 | 5/2013 | Snodgrass |
| 2013/0127615 A1 | 5/2013 | Snodgrass |
| 2014/0009292 A1 | 1/2014 | Long et al. |
| 2014/0035744 A1 | 2/2014 | Wildman |
| 2014/0049391 A1 | 2/2014 | Bolling et al. |
| 2014/0070950 A1 | 3/2014 | Snodgrass |
| 2014/0081653 A1 | 3/2014 | Davis et al. |
| 2014/0292518 A1 | 10/2014 | Wildman |
| 2014/0297327 A1 | 10/2014 | Heil et al. |
| 2014/0320290 A1 | 10/2014 | Reeder et al. |
| 2017/0032656 A1 | 2/2017 | Morgan et al. |
| 2017/0280949 A1 | 10/2017 | Wildman et al. |

OTHER PUBLICATIONS

WHO Guidelines on Hand Hygiene in Health Care, 2009.*

Ward et al., "Automated and Electronically Assisted Hand Hygiene Monitoring Systems: A Systematic Review." American Journal of Infection Control, vol. 42 (May 2014) pp. 472-478.

* cited by examiner

METHODS AND SYSTEMS FOR OBTAINING MORE ACCURATE COMPLIANCE METRICS

RELATED APPLICATIONS

This application claims priority to and the benefits of U.S. Provisional Patent Application Ser. No. 62/079,205 filed on Nov. 13, 2015, entitled "METHODS AND SYSTEMS FOR OBTAINING MORE ACCURATE COMPLIANCE METRICS," which is incorporated herein by reference in its entirety.

BACKGROUND OF THE INVENTION

Traditionally, hand hygiene compliance metrics have been obtained through manual audits and observations. Manual audits and observations suffer from a number of deficiencies. Observers cannot monitor all hand hygiene stations and all personnel all the time. Observed compliancy metrics tend to increase when people know that an observer is watching them and tend to decrease when the observer is not present. In addition, observers randomly choose locations to observe. Accordingly, while compliance metrics in observed areas may increase during manual audits and observations they may only increase at selected sites and for limited times.

Recently, a number of companies have been offering technology-based tools that automatically obtain hand hygiene compliance metrics. These automated electronic hand hygiene compliance monitoring systems receive a signal from the dispenser when the dispenser dispenses a dose of hand cleaner ("a dispense event"). These systems sometimes receive a signal identifying the user that triggers the dispense event. In some cases, another sensor identifies opportunities for a user to wash her hands based on room entry and/or exit events and the number of opportunities are compared to the number of dispense events to arrive at a compliance metric.

The World Health Organization "WHO" has identified five moments when hand hygiene is prescribed: 1) before contact, 2) Before aseptic task, 3) After fluid exposure, 4) After patient contact, and 5) After contact with patient surroundings. Current automated technology-based systems either do not take into effect the five moments, or utilize guesswork to attempt to quantify these 5 moments.

SUMMARY

Exemplary embodiments of methodologies of improving hygiene metric, methodologies of training observers, and software products for improving hygiene metrics are disclosed herein. Exemplary embodiments of methodologies of obtaining more accurate compliance metrics are disclosed herein. An exemplary method of determining a compliance metric includes determining a number of dispense events and determining a number of opportunities for obtaining dispense events. The number of opportunities for obtaining dispense events is a function of the time between an entry event and a exit event, in addition, the compliance metric is a function of the number of dispense events and the number of opportunities.

An exemplary compliance monitoring system includes an area entry sensor for providing a signal indicative of an area entry event, an area exit sensor for providing a signal indicative of an area exit event and a dispenser for dispensing cleaner and providing a signal indicative of a dispense event. The exemplary compliance monitoring system also includes logic stored on a computer readable medium for determining a compliance metric, wherein the compliance metric is a function of the signal indicative of an area entry event, the signal indicative of an area exit event and the signal indicative of a dispense event. In addition, the compliance metric is a function of the time between the area entry event and the area exit event.

Another exemplary method of determining a hand hygiene compliance metric includes obtaining a time stamped signal indicative of an entry event, obtaining a time stamped signal indicative of a dispense event, and obtaining a time stamped signal indicative of an exit event. The exemplary methodology also includes determining a numerator value that is a first value if the time between the entry event and the exit event is greater than a selected time and a second value if the time between the entry event and the exit event is less than the selected time, determining a denominator that is a function of dispense events and calculating a compliance metric that is a function of the numerator over the denominator.

BRIEF DESCRIPTION OF THE DRAWINGS

These and other features and advantages of the present invention will become better understood with regard to the following description and accompanying drawings in which.

DETAILED DESCRIPTION

The Detailed Description merely describes exemplary embodiments of the invention and is not intended to limit the scope of the claims in any way. Indeed, the invention is broader than and unlimited by the exemplary embodiments, and the terms used in the claims have their full ordinary meaning. Although the exemplary embodiments shown and described herein relate to hospital environments, the inventions disclosed herein are equally applicable to other industries, such as, for example, nursing homes, food preparation and processing industries, restaurants, electronics manufacturing and the like. Accordingly, the inventions claimed herein are not limited by the exemplary embodiments, but rather encompass any industry or facility that desires to increase hand hygiene performance.

Figure 1:
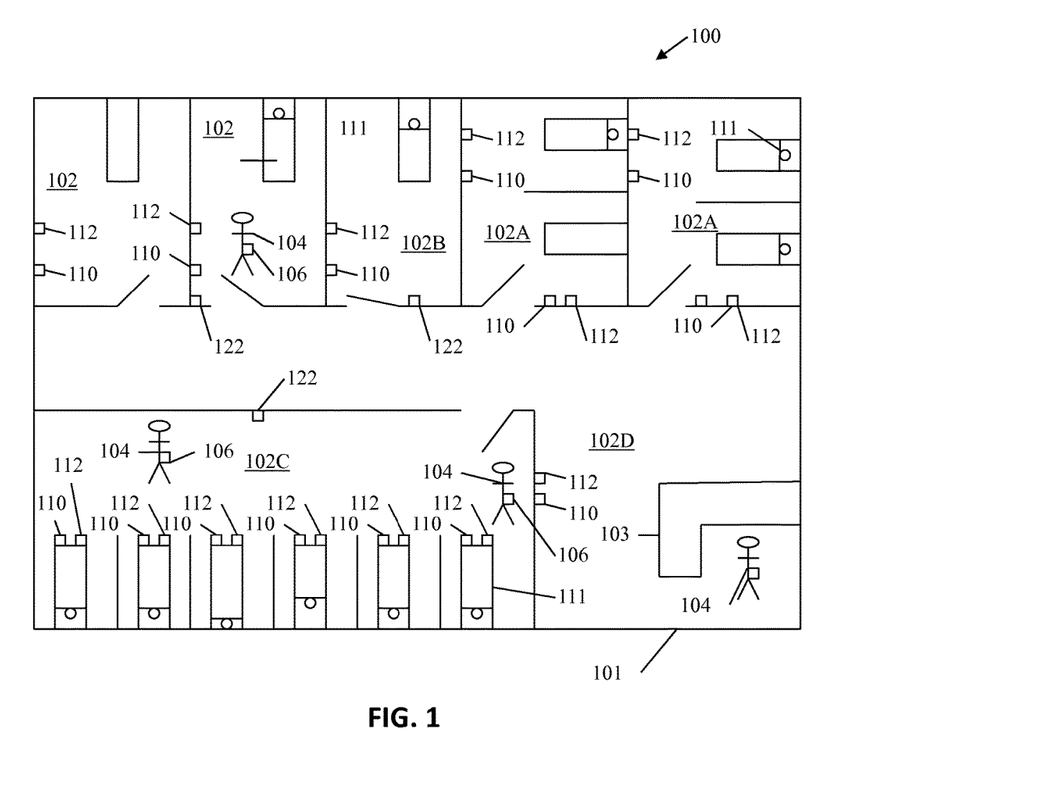
FIG. 1 is a schematic diagram of an exemplary embodiment of an electronic automated monitoring system.

FIG. 1 is a schematic diagram of an exemplary embodiment of an electronic automated monitoring system 100. FIG. 1 illustrates a floor 101 of a hospital. The hospital floor 101 includes a plurality of rooms 102. Several of the rooms are double occupancy rooms 102A. Some of the rooms are single occupancy rooms 102B. One room is a critical care ward 102C and one area is the nurse station 102D. Although the exemplary embodiments described herein relate to hospital environments, the exemplary embodiments may be used in any environment where hand hygiene is important, such as, for example, a food preparation environment.

The automated electronic monitoring system 100 portion includes opportunity sensors 110. Opportunity sensors 110 may be any type of sensor such as a motion sensor, an infrared sensor, a photo-emitter/receiver combination, a radio frequency sensor, or the like. Opportunity sensor 110 detects "entries" and "exits" of the patient caregiver 104 into a patient area. In some embodiments, opportunity sensor may include an optical system, such as, for example, a camera and the opportunities may be obtained through use of analytical software that analyses the captured images to electronically identify opportunities. Similarly, the optical system may be used to electronically identify dispense events.

Opportunity sensor 110 includes circuitry to send an opportunity signal via a transmitter (not shown) to a computer (not shown). The opportunity signal may be sent directly to the computer. In some embodiments, it may be sent to a dispenser 112 which sends it to the computer. Optionally the opportunity signal may be sent via another transmitter or communication device. The opportunity sensor may send an "entry" signal, an "exit" signal, an entry time stamp, an exit time stamp, one or more signals identifying a particular care giver 104, or the like. In some embodiments, only the "entry" signal or "exit" signal is sent to the computer and the computer stamps the time entry upon receipt of the signal.

Dispenser 112 includes dispense event circuitry that sends a dispense signal back to the computer that indicates a dispense event has occurred and also may identify the dispenser with a unique ID. The signal back to the computer may include one or more dispense events and the time, or a "time stamp," of the one or more dispense events. Optionally, the computer that receives the dispense events may log a time of receipt.

In this exemplary embodiment, an opportunity sensor 110 and dispenser 112 are located proximate the nurse station 103, and proximate each patient bed 111. Accordingly, an opportunity exists every time caregiver 104 enters or exits a room, approaches or leaves a patient bed a patient, or enters and leaves the nurse station 102D.

In some embodiments, caregiver 104 carries a badge 106. Badge 106 may include a wireless transmitter (not shown) that transmits a unique ID so that computer may determine which caregiver 104 assigned to badge 106 triggered the opportunity event or dispense event. The term badge as used herein is not limited to standard badges, but rather includes any device that is configured to provide a user's identification, such as, for example, a bracelet, a card, a necklace, Google glasses, a tag, a bar code, and the like. In some embodiments, a biometrics sensor (not shown) is included to determine the identity of a caregiver 104. The biometrics sensor (not shown) may include, for example, optics for facial recognition, vein recognition, retina recognition, finger print recognition or circuitry for any other type of biometric data.

A compliance metric or ratio, i.e. ratio of hand hygiene events divided by hand hygiene opportunities can be calculated by dividing the number of soap or sanitizer dispenses by an estimate of the number of WHO moments. The number of WHO moments opportunities may be estimated by counting room entries and adding a factor "M" for each room visit lasting over a set time threshold. The factor "M" may be based on data associated with set parameters that correlate to the room or area. Different types of room, such as, for example, an Intensive Care Unit 102C may have a different factor "M" than a maternity room 102B. The number of days a patient has been in the room, post operation, diagnosis or any other relevant information that would lead to different levels of patient interaction. For example, the factor M may be assigned the value 2.0 in an ICU; where significant patient interaction is expected. M may be 1.2 for the third day of patient occupancy in a recovery room; when there is little interaction with the patient.

When a user or caregiver 104 enters into room 102, opportunity sensor 110 determines that an entry event has occurred. The entry event may be directly correlated to WHO moment No. 1, which is that a hand hygiene opportunity (an opportunity for caregiver 104 to receive a dose of hand cleaner) has occurred before contact with the patient. The term "hand cleaner," as used herein may be any type of hand cleaner, such as, for example, soap, antibacterial soap, sanitizer, and the like. Similarly, when opportunity sensor 110 determines that an exit event has occurred, the exit event may be directly correlated to WHO moments Nos. 4 and 5, which are hand hygiene opportunities (an opportunity for caregiver 104 to receive a dose of hand cleaner) that occurred after contact with the patient or patient surroundings. As described in more detail below, the exemplary methodologies estimate the occurrences of WHO moments No. 2 and No. 3. The estimate is based on the length of time between room entry and exit, and parameters associated with the room, or assigned patient, that correlates to the occurrences of moments No. 2 and 3. It has been determined that the length of time a caregiver 104 is with a patient, is correlated to the types of activities that the care giver 104 is undertaking.

Exemplary methodologies for improving hand hygiene metrics are disclosed herein. Although the blocks and methodologies below are shown and described in a certain order, the exemplary steps may be completed in different orders, different combinations, with additional steps and/or without certain steps, all of which are included in the scope of the present invention.

Figure 2:
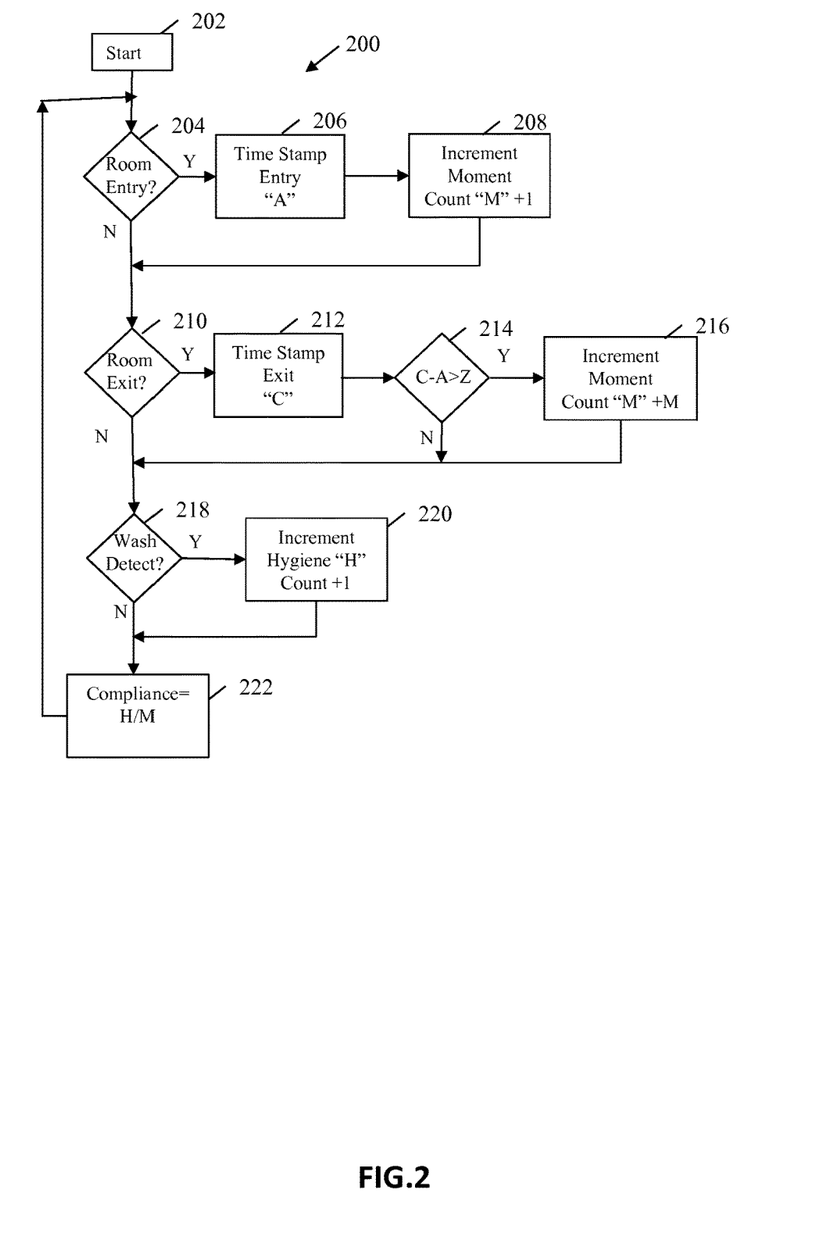
FIG. 2 is an exemplary methodology of obtaining more accurate hand hygiene compliance metrics.

FIG. 2 illustrates an exemplary methodology 200 for estimating hand hygiene compliance metrics which more closely correlates to the WHO 5 moments. The exemplary methodology 200 begins at block 202. At block 204 a determination is made as to whether a hand hygiene opportunity has occurred. In the exemplary methodology, the opportunity is represented by a room entry. If a room entry is detected at block 204, an entry time stamp "A" is recorded. Moment count "M" is incremented by 1 at block 208. Moment count "M" is a preselected number based on the type of room or area that the care giver entered. For example, in a post operation ward, "M" may be determined to be a 3, while for a maternity ward, "M" may be determined to be a 1.

After M is incremented at block 208, or no room entry is detected at block 204, a determination is made at block 210 as to whether a opportunity has been detected at block 210. In this embodiment, the opportunity event is a room exit. If a room exit has been detected at block 210, an "exit" time stamp "C" is stored or logged. At block 214, the time between the room entry event "A" and the room exit event "C" is calculated. If the time between time stamp A and time stamp B is greater than a predetermined time "Z", moment count M is incremented by +M (the preselected M value) at block 216.

After incrementing the value M at block 216, or if the time between the room entry event time stamp A and the room exit event time stamp C is less than time Z at block 214, or if no room exit was determined at block 210, the methodology determines whether a hand wash event or dispense event has been detected at block 218. If a hand wash event was detected at block 218, the Hygiene count "H" is incremented by +1. If no hand wash is detected at block 218, or H was been incremented at block 220, a compliance metric is calculated at block 222 by dividing value H by the accumulated value M. The exemplary methodology loops back to block 204 to determine if a room entry event has occurred, and the compliance metric is continually updated.

Figure 3:
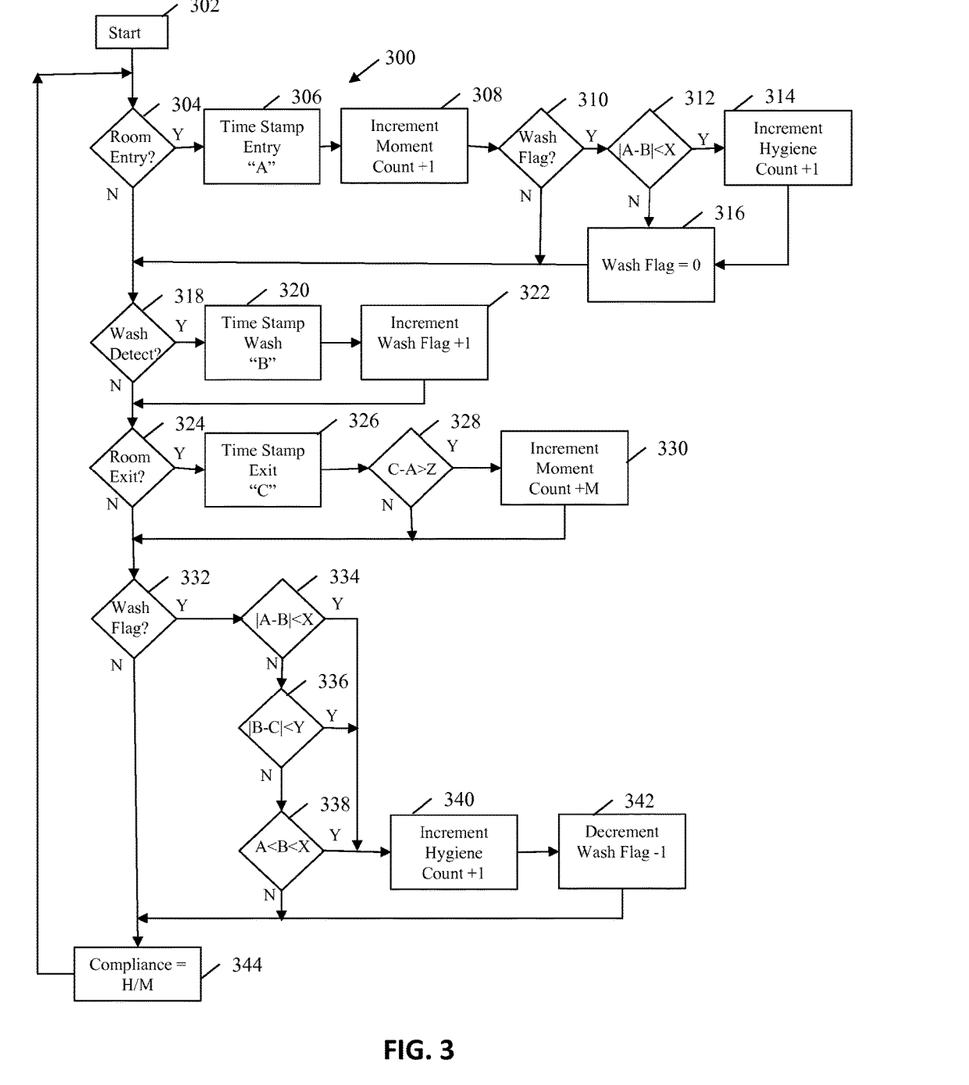
FIG. 3 is another exemplary methodology of obtaining more accurate hand hygiene compliance metrics.

FIG. 3 is a block diagram of another exemplary methodology 300 for estimating hand hygiene compliance metrics that are aligned with the WHO 5 moments. The methodology begins at block 302 and at block 304 a determination is made as to whether an opportunity event, such as a room entry event, has been detected. If an event has been detected at block 304, a timestamp entry "A" is logged at block 306 and at block 308 Moment Count "M" is incremented by +1. As discussed above, "M" may be initially set based on the area that has been entered.

At block 310 a determination is made as to whether a dispense event has occurred, by looking to see if a wash flag is present. Although the first pass through the methodology would typically not have a wash flag set, in some embodiments, an initial wash flag may have been set, on for example, a caregiver's badge, if the caregiver cleaned her hands within a predetermined time frame prior to entering the room, or because a first pass of the methodology has already occurred and the care giver has washed her hands. The term "cleaned" includes washing and/or sanitizing and the term wash includes sanitize. If no wash flag is present at block 310 the methodology flows to block 318. If a wash flag is detected at block 310, a determination is made at block 312 as to whether the absolute value of time between time stamp entry A and time stamp entry B (wash) is less than X. For example, a hospital may require that a health care worker wash within 20 seconds of entering a patient room (either before or after the actual entry).

If the caregiver cleaned her hands within the predetermined time frame X, the hygiene count "H" is incremented by 1 at block 314. After incrementing the hygiene count at block 314, or if the period of time at block 312 is greater than time X, the wash flag is set to 0 at block 316 and a determination is made at block 318 as to whether a hand wash has been detected. If a hand wash is detected, a wash time stamp "B" is logged at block 320 and the wash flag is incremented +1 at block 322.

A determination is made at block 324 as to whether an opportunity event (a room exit) has occurred. If a room exit event has occurred, an exit time stamp "C" is logged and a determination is made at block 328 as to whether the time period between the room exit stamp C and the room entry stamp A is greater than a preselected time Z at block 328. For example if the duration of the room visit is over 120 seconds in a maternity ward, it is assumed that there was patient contact. Observational surveys and historical information could be used to set the various Z thresholds. If the time period is greater that time Z, moment count M is incremented by +M at block 330. If the time period is less than time Z, or M has been incremented at block 330, a determination is made as to whether a opportunity has been detected at block 324. In this embodiment, the opportunity event is a room exit. If a room exit has been detected at block 324, an "exit" time stamp "C" is stored. At block 326, the time between the room entry event "A" and the room exit event "C" is calculated. If the time is greater than a predetermined time "Z" Moment Count M is incremented by +M (the preselected M value) at block 330.

After incrementing M at block 330, or if the time between the room entry event A and the room exit event C is less than time Z at block 328, or no room exit was determined at block 324, the methodology determines whether a wash flag is present at block 332. If no wash flag has been detected, compliance rate metric is calculated at block 344 by dividing the accumulated H value by the accumulated M value. If a wash flag is present at block 332, a determination is made at block 334 as to whether the absolute value of time A-time B is less than time X. If the time is less than time X, the methodology moves to block 340. If it is greater than time X, a determination is made as to whether the absolute value of time B-time C is less than time Y. If the time is less than time Y, the methodology moves to block 340. If it is greater than time Y, a determination is made as to whether time A is less than time B and time B is less than time X. If it is, the methodology moves to block 340 where the hygiene count "H" is incremented by 1. The wash flag count is decremented by 1 at block 342. Once the wash flag is decremented by 1 at block 342, or time A<time B<time X at block 338, the methodology moves to block 340 and calculated the compliance metric by dividing accumulate value of H by accumulated value of M. The methodology loops back to determining whether a room entry has occurred at block 304.

In some embodiments, each time the dispenser dispenses a product, the wash flag is a counter and the count is incremented upward once. In some embodiments, the wash flag is only incremented upward once. In some embodiments, the wash flag is incremented upward again only if the time period between dispense events is greater than a set threshold.

Figure 4:
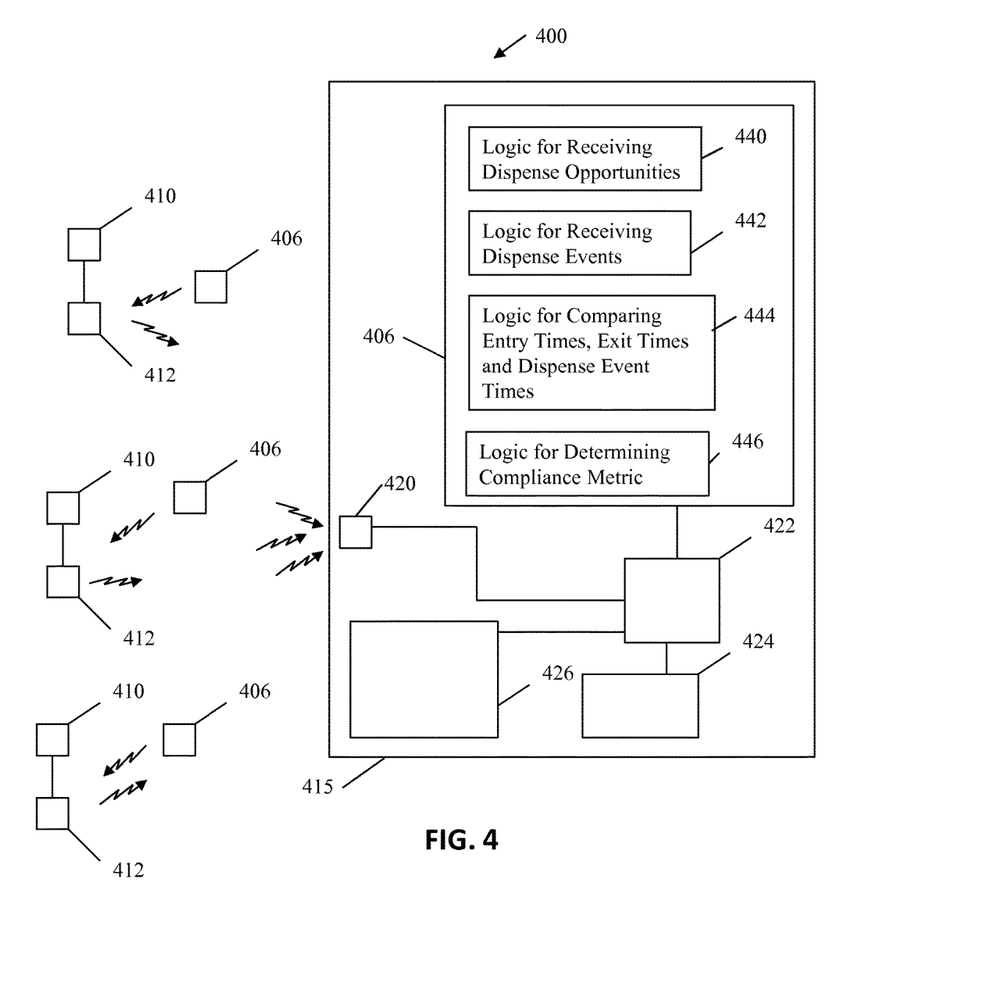
FIG. 4 is an exemplary embodiment of a system for obtaining more accurate hand hygiene compliance metrics.

FIG. 4 is a schematic diagram of an exemplary embodiment of a system 400 that includes a software product for a monitoring system. System 400 includes a plurality of opportunity sensors 410. Opportunity sensors 410 are in circuit communication with dispenser 412. The opportunity sensors 401 determine one or more entries into an area and one or more exits into an area. The entry event signals and exit event signals are transmitted to monitoring station 415. The entry and exit event signals may contain time stamps, or time stamps may be applied to the signals when they reach monitoring station 415. In some embodiments, dispenser 412 includes a transmitter for transmitting a signal indicative of dispense events to monitoring station 415, and in some embodiments a signal indicative of the unique ID for a user is provided to the dispenser 412 by a badge 406. Badge 406 includes a transmitter that transmits a signal to dispenser 412 to provide a unique ID to dispenser 412. In some embodiments, badge 406 has a transmitter that transmits a signal to monitoring station 415. Monitoring station 415 includes a receiver 424 for receiving signals from a plurality of dispensers 412 and/or a plurality of badges 406 and/or a plurality of opportunity sensors 410. Monitoring station 415 includes a processor 422 that is in circuit communication with receiver 420, display 6426, user input 424 and memory 406.

"Circuit communication" as used herein indicates a communicative relationship between devices. Direct electrical, electromagnetic and optical connections and indirect electrical, electromagnetic and optical connections are examples of circuit communication. Two devices are in circuit communication if a signal from one is received by the other, regardless of whether the signal is modified by some other device. For example, two devices separated by one or more of the following—amplifiers, filters, transformers, optoisolators, digital or analog buffers, analog integrators, other electronic circuitry, fiber optic transceivers or satellites—are in circuit communication if a signal from one is communicated to the other, even though the signal is modified by the intermediate device(s). As another example, an electromagnetic sensor is in circuit communication with a signal if it receives electromagnetic radiation from the signal. As a final example, two devices not directly connected to each other, but both capable of interfacing with a third device, such as, for example, a CPU, are in circuit communication.

Memory 406 may be any type of memory such as for example, Random Access Memory (RAM); Read Only Memory (ROM); programmable read-only memory (PROM), electrically programmable read-only memory (EPROM), electrically erasable programmable read-only memory (EEPROM), magnetic disk or tape, optically readable mediums including CD-ROM and DVD-ROM, or the like, or combinations of different types of memory. In some embodiments, the memory 406 is separate from the processor 422, and in some embodiments, the memory 406 resides on or within processor 422.

Located in memory 406 is logic 440 for receiving data indicative of opportunities. In addition, located in memory 406 is logic 442 for receiving data indicative of dispense events for. Logic 444 is included for comparing entry times, exit times and dispense event times. In addition, memory 406 includes logic 446 for determining hand hygiene compliance rates or metrics based on times related to opportunities and dispense events.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

I claim:

1. A method of determining a hand hygiene compliance metric comprising:

providing an area entry sensor;

receiving a signal from the area entry sensor that is indicative of an area entry event by a person;

providing an area exit sensor;

receiving a signal from the area exit sensor indicative of an area exit event by a person;

determining a number of dispense events by receipt of signals from one or more dispensers;

determining a number of hand hygiene opportunities for obtaining dispense events that occur between an entry event signal and an exit event signal from one or more sensors;

wherein the number of hand hygiene opportunities for obtaining dispense events occurs between and is a function of the time between an entry event and an exit event; and wherein the number of hand hygiene opportunities is incremented by a value M, which is greater than 1 if the time between an entry opportunity and an exit opportunity is greater than a selected time period; and providing a hand hygiene compliance metric that is a function of the number of dispense events and the number of hand hygiene opportunities.

2. The method of claim 1 wherein the value of M is a function of the type of area where the entry event occurs.

3. The method of claim 1 wherein the value of M is a function of the days a room is occupied.

4. The method of claim 1 wherein the value of M is a function of the number of patients in a room or area.

5. The method of claim 1 wherein the entry event occurs in an area of a hospital.

6. The method of claim 5 wherein the entry event is a critical care ward.

7. A hand hygiene compliance monitoring system comprising: an area entry sensor for providing a signal indicative of an area entry event by a person; an area exit sensor for providing a signal indicative of an area exit event by a person; a dispenser for dispensing cleaner and providing a signal indicative of a dispense event; wherein the dispense event occurs between the area entry event and the area exit event; logic stored on a computer readable medium for determining a hand hygiene compliance metric, wherein the hand hygiene compliance metric is a function of the signal indicative of an area entry event, the signal indicative of an area exit event and the signal indicative of a dispense event; and wherein the hand hygiene compliance metric is a function of the time between the area entry event and the area exit event; and wherein a variable M is used in calculating the compliance metric and M is increased by more than 1 if the time period between an entry event and an exit event is greater than a selected period of time; and providing an output Cigna signal that is indicative of the hand hygiene compliance metric.

8. The monitoring system of claim 7 further comprising a badge, wherein the badge is associated with a caregiver.

9. The monitoring system of claim 7 wherein M is determined as a function of the type of area where the entry event occurred.

10. The method of claim 7 wherein the value of M is a function of the days a room is occupied.

11. The method of claim 7 wherein the value of M is a function of the number of patients in a room or area.

12. The monitoring system of claim 9 wherein the type of area is an area in a hospital.

13. A method of determining a hand hygiene compliance metric comprising:

providing an area entry sensor;

providing an area exit sensor;

providing a dispenser that provides a signal indicative of a dispense event;

obtaining a time stamped signal indicative of an entry event by a person from the entry sensor;

obtaining a time stamped signal indicative of a dispense event from the dispenser;

obtaining a time stamped signal indicative of an exit event by a person from the exit sensor;

determining a denominator value that is a first value if the time between the entry event and the exit event is greater than a selected time and a second value if the time between the entry event and the exit event is less than the selected time;

determining a numerator that is a function of dispense events;

outputting a hand hygiene compliance metric that is a function of the numerator and the denominator.

14. The method of claim 13 wherein the selected time is a function of the area where the entry event occurs.

15. The method of claim 13 wherein the selected time is a function of the days a room is occupied.

16. The method of claim 13 wherein the selected time is a function of the number of patients in a room or area.

17. The method of claim 13 wherein a dispense event is not included in the denominator if the dispense event occurs after a selected amount of time after an exit event occurred.

* * * * *